(12) United States Patent  
Wada et al.

(10) Patent No.: US 6,540,729 B1
(45) Date of Patent: Apr. 1, 2003

(54) MEN'S DISPOSABLE URINE HOLDING BAG

(75) Inventors: Ichiro Wada, Kagawa-ken (JP); Kozo Abe, Kagawa-ken (JP); Noriyuki Kurita, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 265 days.

(21) Appl. No.: 09/715,405

(22) Filed: Nov. 17, 2000

(30) Foreign Application Priority Data

Nov. 19, 1999 (JP) .......................................... 11-329518
Nov. 2, 2000 (JP) ........................................ 2000-336564

(51) Int. Cl.$^7$ ................................................. A61F 5/453
(52) U.S. Cl. .................................... 604/349; 604/355
(58) Field of Search ..................... 604/327, 346–353, 604/355; 122/DIG. 24; 383/200, 108, 113, 107; 224/148.1

(56) References Cited

U.S. PATENT DOCUMENTS

| | | | | |
|---|---|---|---|---|
| 3,707,969 A | * | 1/1973 | Sanford ....................... 128/287 |
| 4,668,229 A | * | 5/1987 | Fago et al. .................. 604/327 |
| 4,710,188 A | * | 12/1987 | Runeman ................ 604/385 R |
| 4,772,280 A | | 9/1988 | Rooyakkers | |
| 4,790,834 A | * | 12/1988 | Austin ......................... 604/349 |
| 4,790,835 A | * | 12/1988 | Elias ........................... 604/349 |
| 4,886,509 A | * | 12/1989 | Mattsson ..................... 604/349 |
| 5,342,332 A | * | 8/1994 | Wheeler ...................... 604/349 |
| 5,735,837 A | * | 4/1998 | Ishikawa ................. 604/385.1 |
| 5,745,926 A | * | 5/1998 | Cailleteau ....................... 4/144 |
| 5,827,250 A | * | 10/1998 | Fujioka et al. .............. 604/349 |
| 6,059,762 A | * | 5/2000 | Boyer et al. ................. 604/349 |
| 6,209,142 B1 | * | 4/2001 | Mattsson ........................ 2/403 |
| 6,338,729 B1 | * | 1/2002 | Wada et al. ........... 604/385.09 |
| 6,430,755 B1 | * | 4/2002 | Smith .......................... 4/144.2 |
| 6,416,500 B1 | * | 7/2002 | Wada et al. ................. 604/349 |

FOREIGN PATENT DOCUMENTS

| | | | | |
|---|---|---|---|---|
| EP | 0 787 473 A1 | 8/1987 | | |
| EP | 0 841 156 A1 | 5/1998 | | |
| JP | 60-69114 | 5/1985 | ............. | A61F/5/44 |
| JP | 11-140706 | 5/1999 | | |
| WO | WO 89/11839 | * 12/1989 | ........... | A61F/4/435 |
| WO | WO 99/33422 | 7/1999 | | |

* cited by examiner

Primary Examiner—Dennis Ruhl
Assistant Examiner—Michael G. Bogart
(74) Attorney, Agent, or Firm—Baker & Daniels

(57) ABSTRACT

A men's disposable urine holding bag that includes a base sheet which is intermittently bonded to define a bond zone along transversely opposite side edges thereof which edges are placed flat together so as to define an opening for receiving a penis. A body fluid absorbent panel is attached to an inner side of the base sheet. The bond zone has a water pressure resistance of about 50 to 1500 mm.

7 Claims, 5 Drawing Sheets

MEN'S DISPOSABLE URINE HOLDING BAG

BACKGROUND OF THE INVENTION

This invention relates to a men's disposable urine holding bag adapted to be suitably used by, for example, bedridden patients, aged men or incontinent patients.

Japanese Utility Model Application Disclosure No. 1985-69114 describes a men's disposable urine holding bag dimensioned to be longitudinally long and comprising a liquid-pervious topsheet, a liquid-impervious backsheet and a liquid-absorbent core disposed between these two sheets. The bag is formed at its upper end with a penis insertion mouth and the penis is inserted into the bag through the insertion mouth.

In the bag disclosed in the aforesaid Disclosure, the portions of the top- and backsheets extending outward beyond the peripheral edge of the core are continuously bonded together along the bond zone extending along the longitudinally opposite ends as well as the transversely opposite side edges of the bag by means of hot melt adhesive or heat-sealing technique. Such continuously bonded periphery creates a feeling of discomfort and irritation against the wearer when the bonded periphery is in contact with the wearer, since the bonded periphery might be excessively hardened, depending on a width of the bonded periphery.

SUMMARY OF THE INVENTION

An object of the invention is to provide a men's disposable urine holding bag that is designed so as to be free from a possibility that a bond zone of the bag might create a feeling of discomfort and irritation against the wearer and an amount of discharged urine might leak out through the bond zone.

According to this invention, there is provided a men's disposable urine holding bag comprising: a flexible liquid-impervious base sheet; a mouth for insertion of the penis defined by bonding transversely opposite side edges of the base sheet; a body fluid absorbent panel attached to an inner side of the base sheet; the side edges of the base sheet being intermittently bonded to define a bond zone along the side edges of the base sheet; and the bond zone having a water pressure resistance of 50–1500 mm.

With the men's disposable urine holding bag according to this invention, there is no possibility that the bond zone of the bag might be excessively hardened and therefore create a feeling of discomfort and irritation against the wearer and an amount of urine having reached the bond zone of the bag might permeate the bond zone.

DETAILED DESCRIPTION OF THE PREFERRED EMBODIMENTS

Details of a men's disposable urine holding bag according to this invention will be more fully understood from the description given hereunder with reference to the accompanying drawings.

Figure 1:
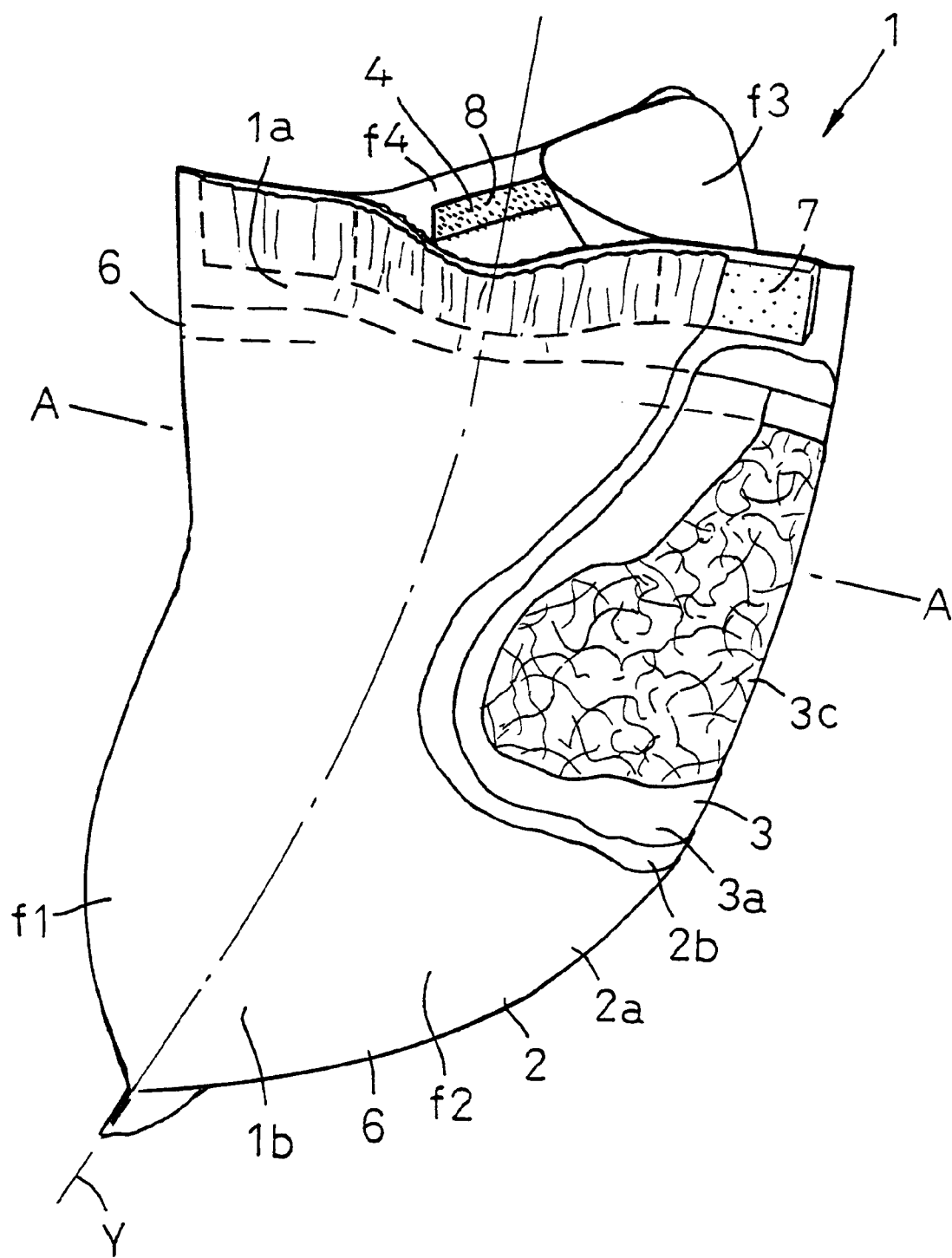
FIG. 1 is a perspective view showing partially cutaway disposable urine holding bag according to this invention as viewed toward its front wall section.
Figure 2:
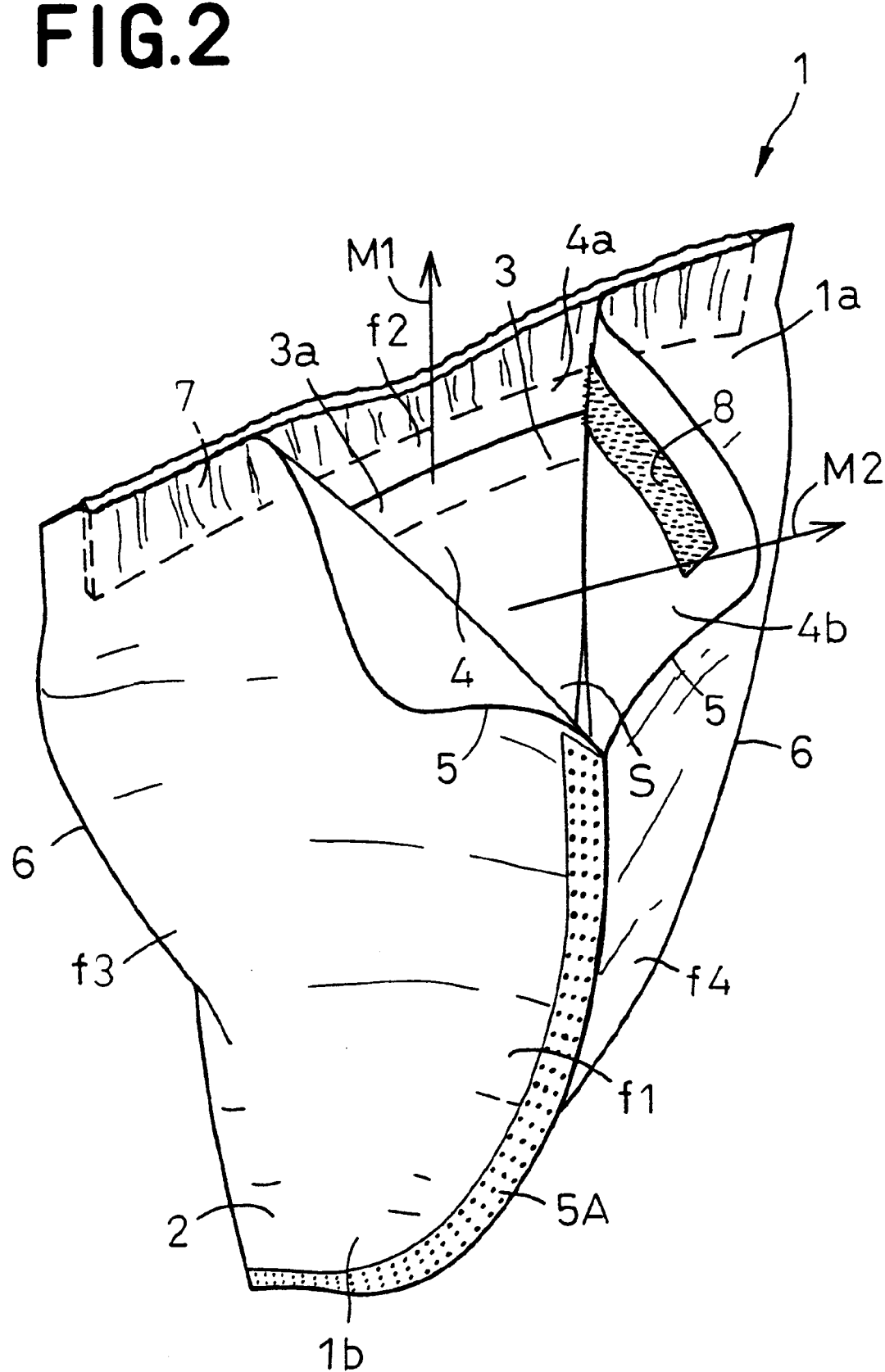
FIG. 2 is a perspective view showing the bag of FIG. 1 as viewed toward its side wall sections.
Figure 3:
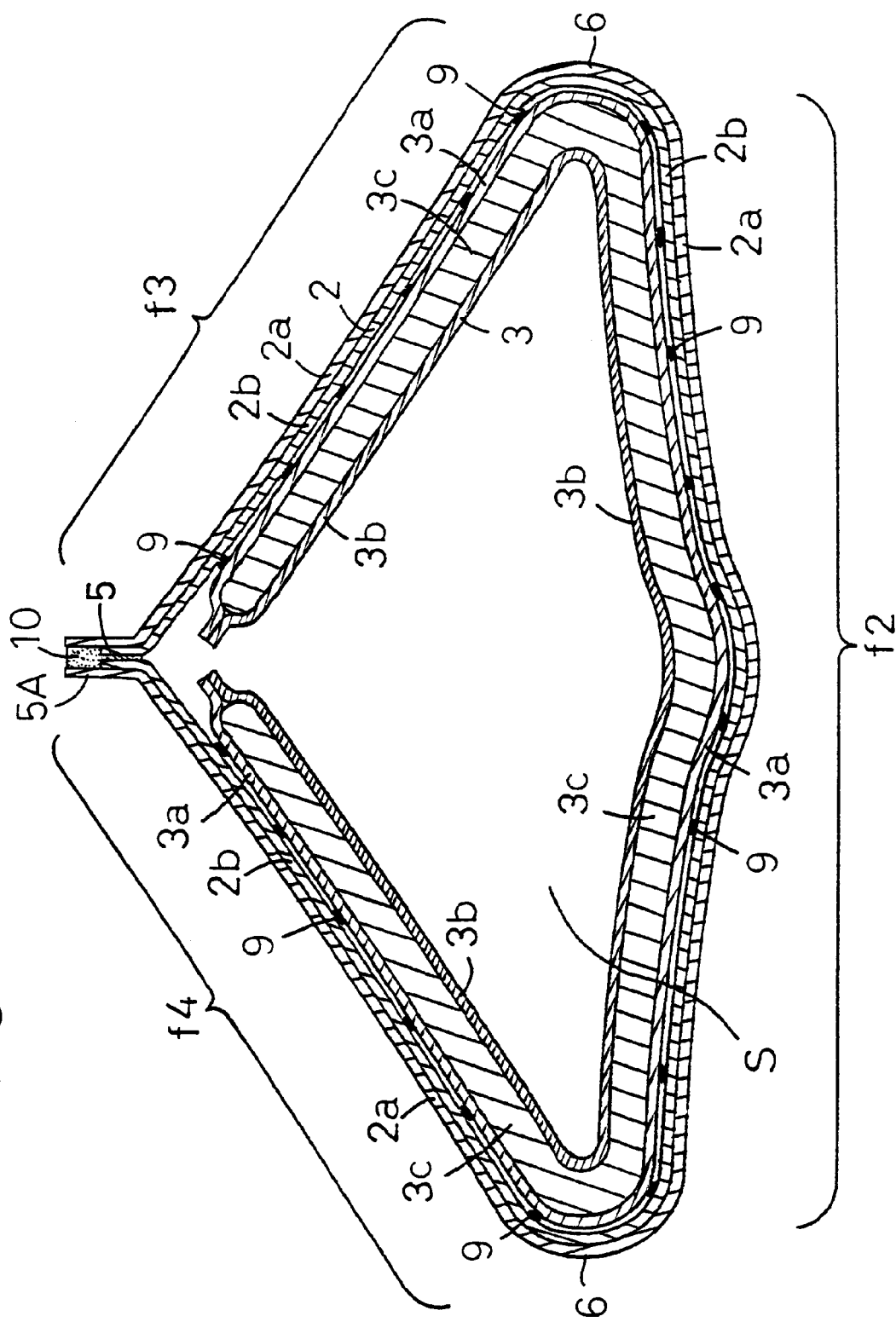
FIG. 3 is a sectional view taken along line A—A in FIG. 1.

FIG. 1 is a perspective view showing a men's disposable urine holding bag 1 according to this invention as viewed toward its front wall section f2, FIG. 2 is a perspective view showing the bag 1 of FIG. 1 as viewed toward its side wall sections f3, f4 with its mouth 4 outstretched and FIG. 3 is a sectional view taken along line A—A in FIG. 1. The bag 1 comprises a flexible and liquid-impervious base sheet 2 serving to maintain a shape of the bag 1 and a relatively flexible body fluid absorbent panel 3 which is attached to the inner surface of the base sheet 2 and consists of cover sheets 3a, 3a and a core 3b. The bag 1 is longitudinally tapered from its upper portion 1a toward its lower portion 1b which is, in turn, further tapered to a point. The bag 1 is provided at the uppermost end of the upper portion 1a with the mouth 4 for insertion of wearer's penis.

The bag 1 is formed by folding the base sheet 2 along a longitudinal center line Y and intermittently bonding transversely opposite side edges 5 of respective halves of the base sheet 2 folded in this manner to each other along transversely opposite side edges 5 of the respective halves of the base sheet 2 longitudinally extending from the upper part toward the lower part of the base sheet 2 so as to describe an arc getting near to the longitudinal center line Y and to define a bond zone 5A.

The base sheet 2 is of a two-layered construction comprising a hydrophobic nonwoven fabric 2a made of thermoplastic synthetic resin fiber and a plastic film 2b made of thermoplastic synthetic resin, the nonwoven fabric 2a lying on the outer side of the bag 1 and the plastic film 2b lying on the inner side of the bag 1. Along the bond zone 5A, the plastic film 2b extends upward as viewed in FIG. 3 and the nonwoven fabric 2a extends further upward than the plastic film 2b also as viewed in FIG. 3. In the bond zone 5A, transversely opposite side edges of the nonwoven fabric 2a as well as the plastic film 2b have their inner surfaces placed upon and a hot melt adhesive 10 is intermittently applied therebetween.

The base sheet 2 has its water pressure resistance of 50–1500 mm along the bond zone 5A. The water pressure resistance along the bond zone 5A lower than 50 mm would cause a problem that the amount of urine discharged might partially permeate the bond zone 5A when urine is collected inside the bond zone 5A. The water pressure resistance higher than 1500 mm is required to use a large quantity of the adhesive 10 and thereby would cause another problem that the base sheet 2 might be excessively hardened along the bond zone 5A and create a feeling of discomfort and irritation against the wearer as the bond zone 5A comes in contact with the wearer.

The plastic film 2b has a water pressure resistance higher than that of the nonwoven fabric 2a. Specifically, the water pressure resistance of the plastic film 2b is in a range of 400–1500 mm while the water pressure resistance of the nonwoven fabric 2a is in a range of 20–100 mm. Even when the water pressure resistance of the nonwoven fabric 2a is insufficient to prevent permeation of urine, the plastic film 2b lying on the inner side of the bag 1 reliably prevents such permeation of urine so far as the plastic film 2b has its water pressure resistance as high as 400–1500 mm.

A peripheral wall f1 of the bag 1 is provided with a pair of fold-guides 6, 6 each longitudinally extending to bisect a dimension between the longitudinal center line Y and the bond zone 5A. The peripheral wall f1 of the bag 1 is folded along the fold-guides 6, 6 to define a front wall section f2 extending between the pair of fold-guides 6, 6 and a pair of side wall sections f3, f4 extending between the bond zone 5A and the respective fold-guides 6, 6. Within the bag 1, the front wall section f2 is spaced from the pair of side wall sections f3, f4 to define a space S.

The mouth of the bag 1 comprises a first mouth region 4a surrounded by respective upper ends of the front wall section f2 and the side wall sections f3, f4 so as to open upwardly of the bag 1 as indicated by an arrow M1 in FIG. 2 and a second mouth region 4b. surrounded by the side wall sections f3, f4 extending from the upper end of the bond zone 5A toward the first mouth region 4a so as to open laterally of the bag 1 in continuity with the first mouth region 4a as indicated by an arrow M2 in FIG. 2. In the mouth 4, the upper end of the front wall section f2 and the respective upper ends of the side wall sections f3, f4 are partially placed upon and bonded to one another in the vicinity of the fold-guides 6, 6. To bond the front wall section f2 to the side wall sections f3, f4, regions in which these wall sections are intermittently bonded one to another preferably have a water pressure resistance of 50–1500 mm substantially the same as that of the bond zone 5A.

In the first mouth region 4a, an elastically stretchable member 7 extending transversely of the bag 1 is bonded under tension to the front wall section f2 along its upper end. The first mouth region 4a is further provided along the upper end of the side wall section f4 with a ribbon-like hook member 8 attached to the inner side of the bag 1 as a component of the well-known mechanical fastener.

The panel 3 comprises the semi-rigid liquid-absorbent core 3b covered with and bonded to the flexible liquid-impervious cover sheets 3a facing the base sheet 2 and to the flexible liquid-pervious cover sheet 3b remote from the base sheet 2. The cover sheet 3a is intermittently bonded to the base sheet 2 by means of an adhesive 9. The panel 3 occupies the front wall section f2 as well as the side wall sections f3, f4 except the first and second mouth regions 4a, 4b as well as the vicinity of the bond zone 5A.

Figure 4:
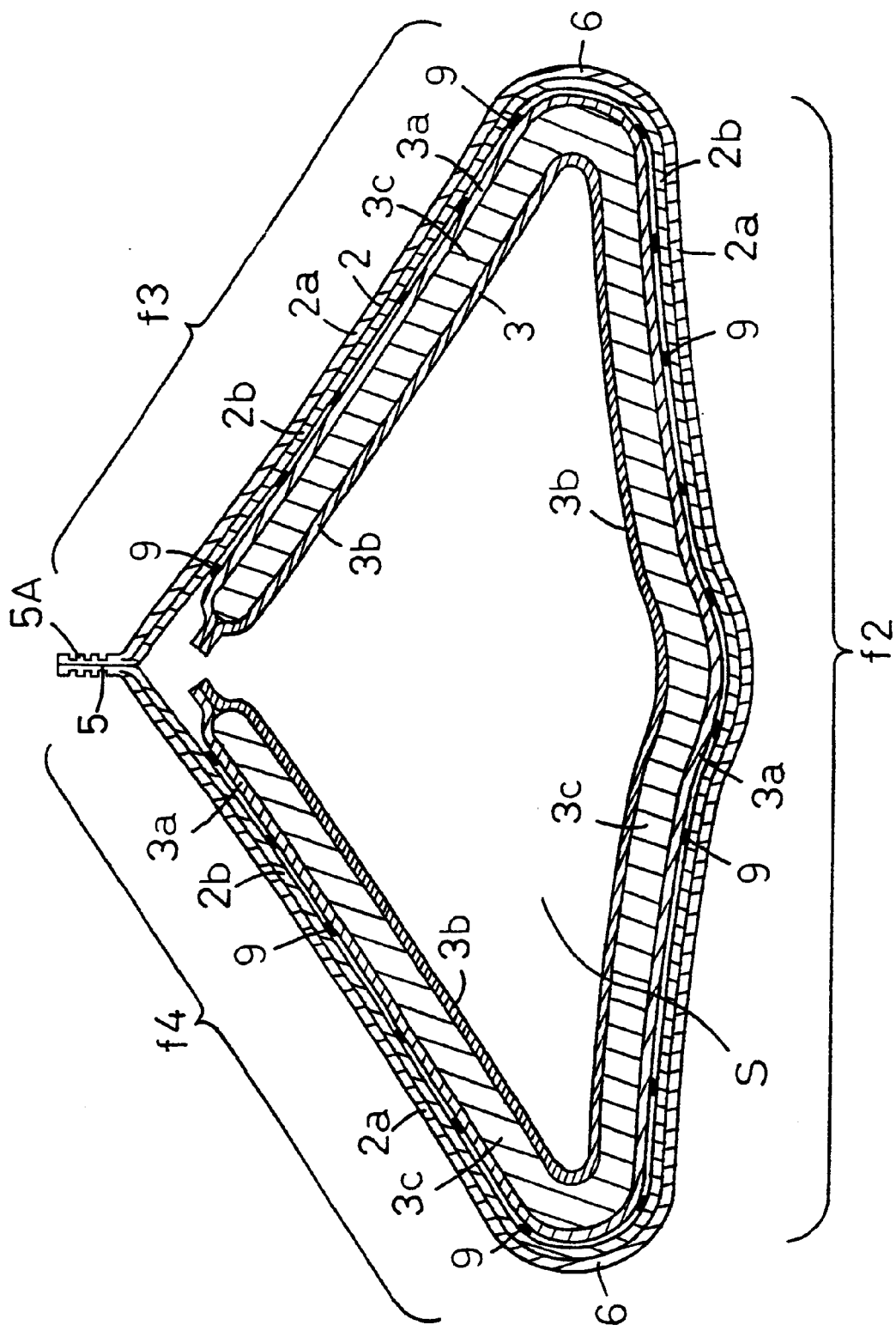
FIG. 4 is a sectional view taken along line A—A in FIG. 1.

FIG. 4 is a view similarly taken along line A—A in FIG. 1 but the bond zone 5A has a configuration different from the bond zone 5A shown in FIG. 3. The base sheet 2 is of a two-layered configuration comprising a hydrophobic non-woven fabric 2a and a plastic film 2b, the nonwoven fabric 2a lying on the outer side of the bag 1 and the plastic film 2b lying on the inner side of the bag 1. The base sheet 2 is intermittently bonded to itself along the bond zone 5A using the well-known sealing technique such as dot-like heat-embossing or sonic-embossing.

The base sheet 2 has a water pressure resistance of 50–1500 mm along the bond zone 5A. The water pressure resistance along the bond zone 5A lower than 50 mm would cause a problem that the amount of urine having reached the bond zone 5A might permeate this bond zone 5A to soak it. The water pressure resistance higher than 1500 mm would cause another problem that the base sheet 2 might be excessively hardened along the bond zone 5A.

The nonwoven fabric 2a has a water pressure resistance of 20–100 mm while the plastic film 2b has a water pressure resistance of 400–1500 mm. In the case of the bag 1 shown in FIG. 4, the plastic film 2b having the water pressure resistance as high as 400–1500 mm. Therefore, the water pressure resistance of the plastic film 2b along the bond zone 5A can be maintained at a level of 50–1500 mm even after the plastic film 2b has been heated and molten along the bond zone 5A in the course of the bonding process.

Figure 5:
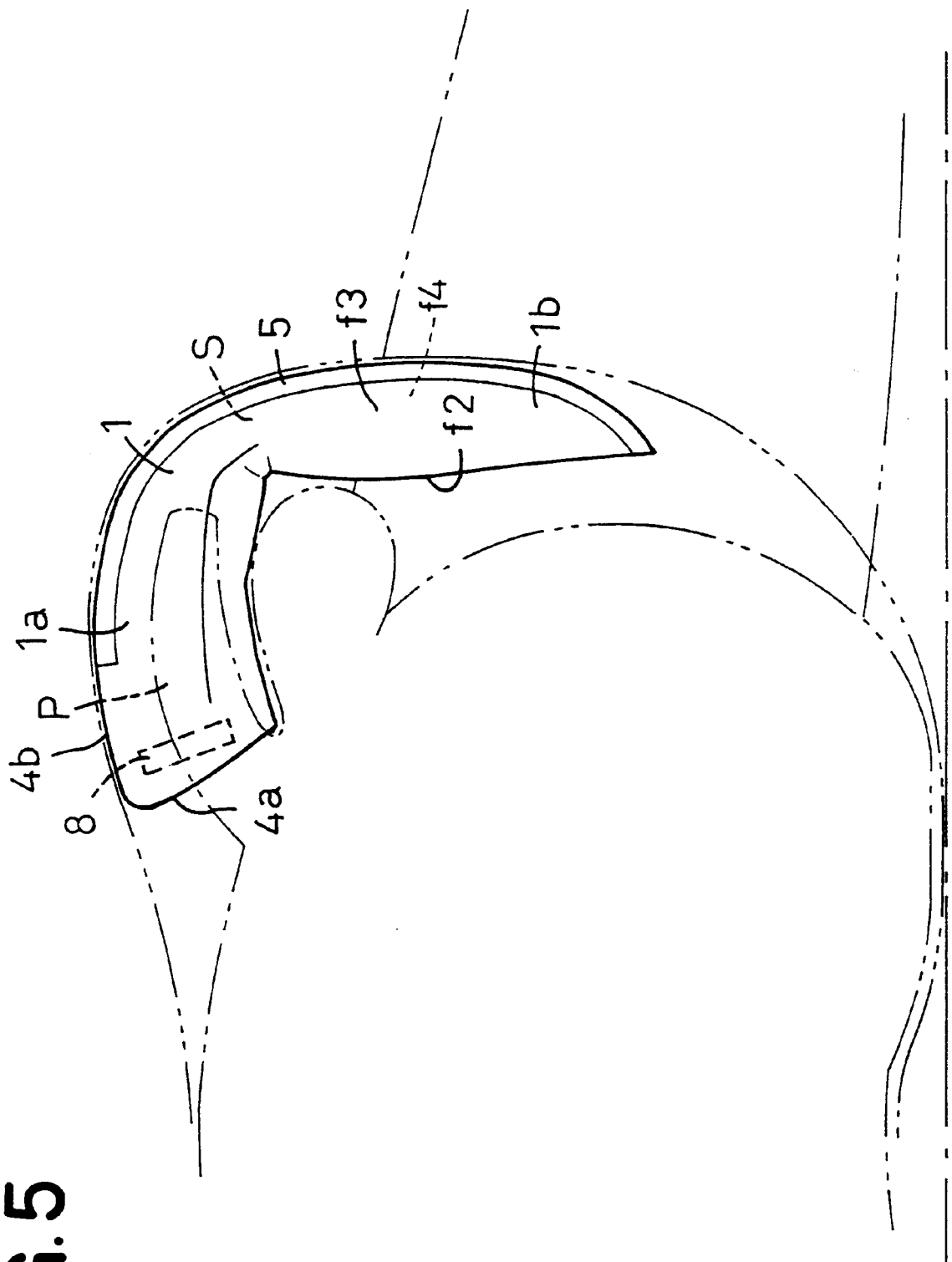
FIG. 5 is a diagram illustrating a manner in which the bag is actually used.

FIG. 5 is a diagram illustrating a manner in which the bag of FIG. 1 is actually used. The upper end of the front wall section f2 is placed around the root of the penis P which is then put into the bag 1 through the first and second mouth regions 4a, 4b. Instead of inserting the penis P directly through the mouth 4, the penis P may be placed in the bag 1 via the mouth regions 4a, 4b to facilitate the operation of inserting the penis P into the bag 1. Once the penis P has been put into the bag 1, the side wall sections f3, f4 are overlapped each other with the side wall section f4 overlying the side wall section f4 to wrap the penis P and the hook member 8 is anchored on the outer side of the side wall section f3.

After the bag 1 has been put on the penis P, the lower part 1b of the bag 1 is positioned in the wearer's crotch region. The lower part 1b of the bag 1 positioned in the wearer's crotch region is smoothly received therein since the bag 1 is tapered from the upper part 1a toward the lower part 1b which is pointed. Specifically, it is the front wall section f2 but not the bond zone 5A of the bag 1 that is placed against the wearer's crotch region.

For the bag 1, it is possible without departing from the scope and spirit of this invention to provide the base sheet 2 in the form of a monolayered flexible hydrophobic non-woven fabric. In the case of such monolayered nonwoven fabric, the synthetic resin fiber forming this nonwoven fabric preferably has its density gradually increasing from the outer side toward the inner side of the bag 1 so that a region of the nonwoven fabric layer lying on the inner side of the bag 1 may have a water pressure resistance of 80–300 mm while a region of the nonwoven fabric layer lying on the outer side of the bag 1 may have a water pressure resistance of 20–100 mm. The region of the nonwoven fabric layer lying on the inner side of the bag 1 with the water pressure resistance of 80–300 mm can reliably prevent urine permeation into the nonwoven fabric. With the arrangement such that the non-woven fabric layer is bonded together along the bond zone 5A by means of the adhesive 10, the region with the water pressure resistance of 80–300 mm can prevent urine exudation into the interface of bonding. In the case of the bond zone 5A along which the nonwoven fabric layer is heat-sealed together, it is reliably achieved to maintain a water pressure resistance of the bag 1 along the bond zone 5A in a range of 50–1500 mm even after the nonwoven fabric layer has been weakened along the bond zone 5A due to heating and melting in the course of the heat-sealing.

For the bag 1, it is also possible without departing from the scope and spirit of this invention to provide the base sheet 2 in the form of two-layered flexible hydrophobic nonwoven fabric. In this case, the nonwoven fabric lying on the inner side of the bag 1 preferably has a density higher than that of the nonwoven fabric lying on the outer side of the bag 1 so that o that the nonwoven fabric layer lying on the outer side of the bag 1 may have a water pressure resistance of 20–100 mm while the nonwoven fabric layer lying on the outer side of the bag 1 may have a water pressure resistance of 80–300 mm. The nonwoven fabric layer lying on the inner side of the bag 1 with the water pressure resistance of 80–300 mm can reliably prevent urine permeation into the base sheet 2. With the arrangement such that the nonwoven fabric layers are bonded together along the bond zone 5A by means of the adhesive 10, the non-woven fabric layer with the water pressure resistance of 80–300 mm can prevent urine exudation into the interface of bonding. In the case of the bond zone 5A along which the base sheet 2 is heat-sealed together, it is reliably achieved to maintain a water pressure resistance of the bag 1 along the bond zone 5A in a range of 50–1500 mm even after the base sheet 2 has been weakened along the bond zone 5A due to heating and melting in the course of the heat-sealing.

Without departing from the scope and spirit of this invention, the base sheet 2 may be provided also in the form of three- or four-layered sheet. In the case of the base sheet 2 comprising a nonwoven fabric and a plastic film placed one upon another in two or more layers, it is preferable to lay the plastic film on the inner side and to lay the nonwoven fabric on the outer side of the bag 1. The plastic film preferably has a water pressure resistance of 400–1500 mm and the nonwoven fabric preferably has a water pressure resistance of 20–100 mm. For the intermediate layer(s) of the base sheet 2, the order in which the nonwoven fabric layer and the plastic film should be placed upon each other is not specified. To configure the three-layered base sheet 2, at least one of the nonwoven fabric layer and the plastic film layer may be laid between the two layers lying on the inner and outer sides of the bag 1, respectively.

In the case of the base sheet 2 comprising two layers of nonwoven fabric placed upon each other, it is preferably to lay the nonwoven fabric layer having its water pressure resistance of 80–300 mm on the inner side of the bag 1 and to lay the nonwoven fabric layer having its water pressure resistance of 20–100 mm on the outer side of the bag 1.

The cover sheet 3a may be formed using a flexible hydrophobic nonwoven fabric or a flexible liquid-impervious plastic film, preferably using a breathable liquid-impervious sheet. The cover sheet 3b may be formed using a flexible liquid-pervious sheet such as a nonwoven fabric or a porous plastic film, preferably using a liquid-pervious hydrophilic sheet.

The nonwoven fabric used for the purposes as have been described above may be selected from a group including an air-through nonwoven fabric, a spun lace nonwoven fabric, a needle punch nonwoven fabric, a melt blown nonwoven fabric, a thermal bond nonwoven fabric, a spun bond nonwoven fabric and a chemical bond nonwoven fabric. The component fiber of the nonwoven fabric may be selected from a group including polyolefine, polyester, polyamide fibers and conjugated fiber such as polyethylene/polypropyrene or polyester.

The core 3c generally comprises a mixture of fluff pulp and superabsorptive hydrogel particles compressed to a desired thickness and entirely covered with a water-pervious sheet (not shown) such as tissue paper. The elastic member 7 may be formed using elastically stretchable formed sheet of polyurethane, synthetic rubber or polystyrene, or an elastically stretchable urethane film.

Bonding of the cover sheets 3a, 3b and the core 3c as well as attaching of the other members such as the elastic member 7 and the hook members 8 may be carried out using an adhesive such as a hot melt adhesive or a pressure-sensitive adhesive or a technique of sonic-sealing or heat-sealing.

The panel 3 may be provided in the form of the core 3c covered with the liquid-impervious cover sheet 3a and the liquid-pervious cover sheet 3b, or in the form of the core 3c wrapped with the liquid-pervious cover sheet 3b or in the form of the core 3c disposed between the base sheet 2 and the liquid-pervious cover sheet 3b.

In addition to the bag 1 having a space within it, this invention is applicable also to the flat bag having upper and lower layers placed upon each other.

What is claimed is:

1. A men's disposable urine holding bag comprising:

a flexible liquid-impervious base sheet;

a mouth for insertion of the penis defined by bonding transversely opposite side edges of said base sheet;

a body fluid absorbent panel attached to an inner side of said base sheet;

the side edges of said base sheet being intermittently bonded to define a bond zone along the side edges of said base sheet; and said bond zone having a water pressure resistance of 50–1500 mm.

2. The bag according to claim 1, wherein the intermittent bond in said bond zone is made by a plurality of adhesives dots.

3. The bag according to claim 1, wherein the intermittent bond in the said bond zone is made by a plurality of heat-embossed dots.

4. The bag according to claim 1, wherein said base sheet comprises hydrophobic nonwoven fabric made of thermoplastic synthetic resin fiber and said synthetic resin fiber has a density gradually increasing from the outer side toward the inner side of said bag.

5. The bag according to claim 1, wherein said base sheet is of at least two-layered configuration comprising a hydrophobic nonwoven fabric made of thermoplastic synthetic resin fiber and a plastic film made of thermoplastic synthetic resin and having a water pressure resistance higher than that of said nonwoven fabric and wherein said nonwoven fabric is laid on the outer side of said bag.

6. The bag according to claim 1, wherein said base sheet is of at least two-layered configuration comprising hydrophobic nonwoven fabric layers each made of thermoplastic synthetic resin fiber and wherein said nonwoven fabric layer defining the inner side of said bag has a water pressure resistance higher than that of said nonwoven fabric layer defining the outer side of said bag.

7. The bag according to claim 1, wherein said bond zone of said bag extends from an upper part toward a lower part of said bag so as to get near to said longitudinal center line to form the bag tapered downward and wherein a peripheral wall of said bag is folded along a pair of fold-guides longitudinally extending to bisect a dimension between said longitudinal center line and said bond zone thereby to divide said peripheral wall into a front wall section extending between said pair of fold-guides and a pair of side wall sections extending between respective said fold-guides.

* * * * *